United States Patent [19]

Hartmann et al.

[11] 4,413,032

[45] Nov. 1, 1983

[54] NON-WOVEN FABRIC WITH WICK ACTION

[75] Inventors: Ludwig Hartmann; Ivo Ruzek, both of Kaiserslautern, Fed. Rep. of Germany

[73] Assignee: Carl Freudenberg, Fed. Rep. of Germany

[21] Appl. No.: 309,223

[22] Filed: Oct. 6, 1981

[30] Foreign Application Priority Data

Nov. 27, 1980 [DE] Fed. Rep. of Germany ....... 3044631

[51] Int. Cl.$^3$ .............................................. D04H 1/58
[52] U.S. Cl. .................................. 428/288; 156/62.2; 156/62.4; 428/289; 428/290
[58] Field of Search ...................... 428/288, 289, 290; 156/62.2, 62.4

[56] References Cited

U.S. PATENT DOCUMENTS 4,363,845 12/1982 Hartmann ........................ 428/288

Primary Examiner—Marion McCamish
Attorney, Agent, or Firm—Keil & Witherspoon

[57] ABSTRACT

A surface treated, non-woven fabric covering for absorbent cellulose materials, and a method for its manufacture, wherein polymer fibers are coated with an effective amount of a wetting agent which can be chemisorbed on cellulose; the addition of the wetting agent taking place before extrusion in the spinning process, or at any point of manufacture including after the non-woven fabric covering has been finished; the wetting agent being, in the preferred embodiment, a cationic surfactant.

5 Claims, No Drawings

NON-WOVEN FABRIC WITH WICK ACTION

The invention relates to a surface-treated non-woven fabric from synthetic fibers with wick action, more particularly for use as a covering non-woven fabric for absorbent layers.

Covering non-woven fabrics from synthetic fibers are already known. They are frequently used, directly or in combination with other materials, for making various sanitary and medical articles. For example, disposable diapers are made from an absorbent layer which essentially consists of cellulose. The absorbent layer is provided with a covering and firm non-woven fabric from synthetic fibers. Bandages as well as feminine-hygiene and surgical tampons have a similar structure. In addition, multilayer flat-shaped articles (composites) are known in which absorbent layers are externally covered with a non-woven fabric, the composites being employed as disposable towels, dishcloths, etc. for household use, in industry or in the clinical field. Finally, such non-woven fabrics are utilized directly or as composites in combination with other composites as materials for making disposable clothing for use in clinics, but also for other purposes.

Non-woven fabrics to be used as covering materials or also directly for these applications must have sufficient mechanical strength, adequate opacity, and a suitability for use in ready-to-wear apparel. It is also essential that the covering non-woven fabrics enable an adequate transport of aqueous liquids or vapors to the absorbent layers.

Covering non-woven fabrics are known and commercially available which have a wick action to ensure the spreading of liquids. Wick action is the ability to be wetted by liquids and at the same time to transport the liquid by capillary action. If the wick action is inadequate, the transport of the liquid is not ensured and the absorptive power of the product is defective.

As a rule, in sanitary and medical composites simple wick action is insufficient, because it is necessary to prevent the liquid stored in the absorbent layer from flowing back, thus creating a "dry" impression. Hence, the wick action in the opposite direction must be reduced, if not completely prevented. That means that the two requisites: primary transport and subsequent blocking action are fully incompatible.

The principal aim of the invention is to develop a non-woven fabric with wick action which fulfills the two requisites. The liquid must be transported very quickly to the absorbent layer and it must be prevented from flowing back, or only insignificantly.

This problem is solved in accordance with the teachings of the invention by a surface-treated non-woven fabric from synthetic fibers with wick action, characterized in that it contains as active substance a wetting agent which acts substantively with respect to cellulose, such that it can be chemisorbed on the cellulose or on the cellulose-containing substrate. A surprising fact found was that the totally incompatible requisites of rapid primary transport to the absorbent pad and blocking action in the opposite direction can be combined to optimum advantage.

For sufficient wick action it is necessary that the surface of the non-woven fabric, or the surface of the fibers forming the same, be first wetted by the liquid. As is known, most synthetic polymers possess a relatively low surface energy, whereas water and most aqueous liquids are characterized by a relatively high boundary surface energy ($72.7 \times 10^{-3}$ N/m). The boundary surface energies of the most important fiber-forming polymers are listed in the table below.

| | critical | Boundary surface energy ($10^{-3}$ N/M) polar portion | dispersed portion |
|---|---|---|---|
| Polyethyleneterephthalate | 47.3 | 4.1 | 43.2 |
| Polyamide | 47.0 | 6.2 | 40.8 |
| Polypropylene | 33.2 | 0.0 | 33.2 |

The value of the maximum boundary surface energy that a liquid can attain and that is still capable of wetting the surface is designated as the critical boundary surface energy. The portion of the total boundary surface energy originating only from dispersion forces is termed the dispersed portion of the boundary surface energy, whereas the portion which is solely caused by the polar interactions is called the polar portion. In the case of water, it is assumed that the predominant portion—approximately $\frac{2}{3}$—is attributable to the polar and only about $\frac{1}{3}$ to the dispersion forces.

The wick action depends upon the capillarity of the porous material and upon its surface energy in relation to those of the liquid to be transported. A difference in the surface energies has a decreasing effect on the porosity. Thus, in a given porous material the wick action can be enhanced by increasing the critical value of the boundary surface energy and its adaptation to the value of the acquous liquid to be transported can be improved. For example, this can be achieved by treating the surface of the non-woven fabric or of the fibers with surfactants. Already known non-ionogenic surfactants possessing an adequate absorptive capacity on the polymer surfaces are suitable as active surfactants.

Very effective are ethoxylated alkylaryl compounds, the action of which can be adjusted to suit their respective applications through appropriate variation of the composition. The wettability of the surface of the non-woven fabric can be improved by the use of such surfactants and the spreading of the liquid across the non-woven fabric is accelerated. This is due to the fact that the adjustment of the surface energies of the non-woven fabric and of the liquid to be spread tend to effectively increase the porosity. Once the total wetting of the surface is accomplished, the liquid can migrate through the capillaries of the absorbent layer. The liquid is then stored in the absorbent layer.

Although the wick action of a non-woven fabric thus treated is excellent, serious problems arise due to the unchecked backflow of the liquid when pressure is exerted against the surface of the absorption pad covered with such non-woven fabric. Immediately the covering non-woven fabric is wetted again with the liquid stored in the absorbent pad. It has a "wet" apperance and the liquid flows back without hindrance in the opposite direction. The improved wettability, which was beneficial to the primary transport of the liquid in the desired direction to the absorbent pad, now becomes an undesirable drawback. Thus, though non-ionogenic surfactants such as normally used as wetting agents in industry permit wick action, they have proved to be unsuitable for the finishing of covering non-woven fabrics, because they remain adsorbed on the surface of the non-woven fabric or of the fibers, thus accelerating the spreading of the liquid in either direction. Hence, the principal aim of the invention is not achieved with conventional non-ionogenic surfactants.

Only a very small portion of non-ionogenic surfactants changes to the liquid phase, if at all. There, too, they fully ensure the maintenance of the wetting action in either direction. If it is desired to reduce the backflow of the stored liquid, an attempt must be made to achieve a state of equilibrium through fine adjustment of the amount of surfactants, taking account of both the primary transport to the absorbent pad and the backflow. If really necessary, a pretty nearly satisfactory result can be achieved through a compromise solution.

Since the primary aim of the invention is to develop a non-woven material which, while exhibiting excellent wick action in the direction of the absorbent pad, prevents the stored liquid to a large extent from flowing back, non-woven fabrics finished with conventional non-ionogenic surfactants cannot solve this problem for the reasons set forth above. However, an optimum solution of the problem is found if surfactants are employed which can be chemisorbed on the cellulose or on the cellulose-containing material of the absorbent pad and which can be transported by the liquid to the absorbent pad.

It has been shown that the totally incompatible requisites of fast primary transport to the absorbent pad and blocking action in the reverse direction can be made compatible. Cationic surfactants having the general formula

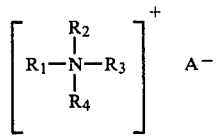

have shown their worth as wetting agents for the covering non-woven fabric, in which $R_1$, $R_2$, $R_3$ and $R_4$ can be alkyl of 1 to 20 carbon atoms, aryl (i.e. phenyl or naphthyl), alkylaryl having 1 to 20 carbon atoms in the alkyl group, ethoxy, akylethoxy having 1 to 20 carbon atoms in the alkyl group, arylethoxy, and/or alkylarylethoxy having 1 to 20 carbon atoms in the alkyl group. The radical A is a conventional anion, e.g., a halide.

It has been found that the cationic surfactants exhibit an outstanding wetting action. They considerably improve the wick action because on the one hand they are adsorbed only weakly by the polymer surface so that a substantial part changes to the liquid phase during the wetting action and, on the other hand, they react substantially with respect to cellulose, that is to say, they are chemisorbed on cellulose-containing substrates and, as a result, are prevented from changing to the liquid phase. Thus, the liquid phase serves as a means for transporting the wetting agent from the inherently water-repellent fibers to the absorbent medium. Therefore, the covering non-woven fabric can be wetted well so as to improve the primary transport, because the adequate amount of the surfactant and subsequent binding to the cellulose-containing substrate act as a blocking layer, preventing the liquid from flowing back. Since the non-woven fabric, which is composed of synthetic fibers, itself absorbs or binds only very little water, it has a "dry" appearance, even if clamped over a moist absorbent pad.

The cationic surfactants proposed by the invention may be applied in large doses. Thus, rapid wetting can be achieved without stimulating a backflow. Optimum properties of the covering non-woven fabric are obtained in terms of the incompatible requisites for the wick and blocking actions.

Furthermore, the cationic surfactants advocated by the invention have the advantage of being bacteriostatic or even bactericidal, which is very desirable for many fields of application, particularly in the medical field. Covering non-woven fabrics finished in accordance with the principles of the invention can unhesitatingly be employed in the clinical and medical fields, as well as in the cosmetic-sanitary area. In this case, it is important that the surfactants have no adverse side effects on the human system.

Among the cationic surfactants proposed by the invention, the following compounds have proved to be very successful:

Stearyldimethylbenzyl ammonium chloride:

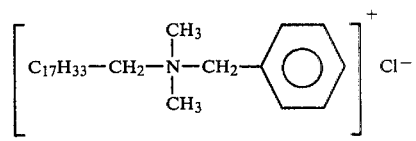

Methyldodecylbenzyltrimethyl ammonium chloride:

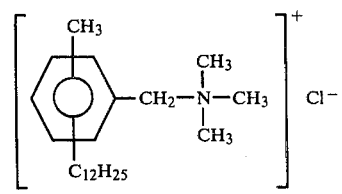

Dodecyldimethylbenzylammonium chloride:

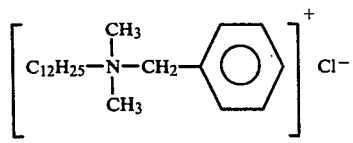

Tetradecyldimethylbenzylammonium chloride:

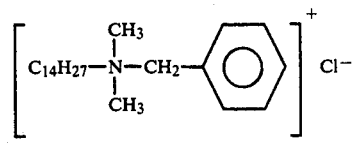

Hexadecyldimethylbenzylammonium chloride:

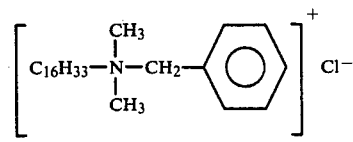

Diisobutylcresoxyethoxyethyldimethylbenzammonium chloride:

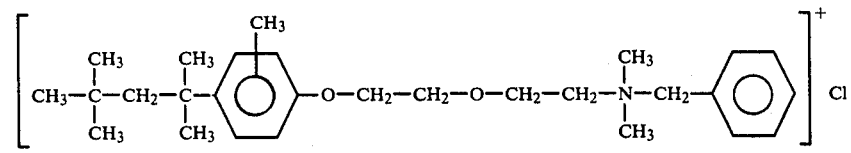

Diisobutylphenoxyethoxyethyldimethylbenzylammonium chloride:

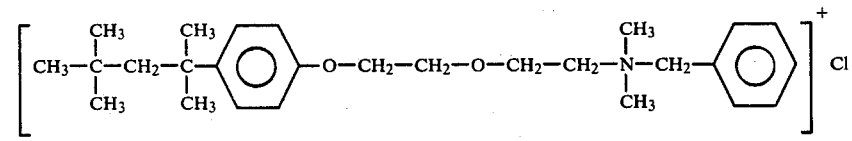

Methyldodecylxylylene-bis-(trimethylammonium chloride):

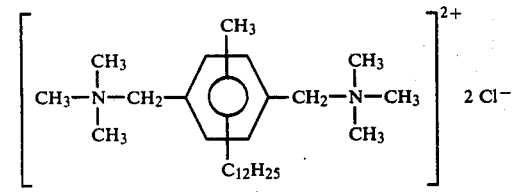

Although any quantitative portions of the cationic surfactants may be used, coating quantities in the range of 0.05-1.0 weight percent in relation to the weight of the non-woven fabric have generally proved to be successful to finish covering non-woven fabrics. Frequently, quantities up to 0.5 weight percent are adequate.

The non-woven fabric can be finished in a manner in itself known by slop-padding, nip-padding, or by spraying the aqueous solutions or by dispersions and subsequent drying, optionally under pressure. Non-woven fabrics of any composition can be treated in this manner. The cationic surfactants may also be added to standard finishing agents and in this way be used in very simple fashion. Advantageously, finishing can be effected by adding a correctly metered quantity of the cationic surfactants to the polymer melt during the spinning process. In this case, the cationic surfactants represent a phase which is foreign to the polymer melt and is immiscible therewith. Because of its low viscosity, this polymer melt is transported to the surface of the fibers.

EXAMPLE 1

A spinning non-woven fabric from polypropylene fibers having a filament titre of 2.2 dtex and a weight per unit area of 15 g/m², bound in accordance with the point calender technique and having a thickness of 0.16 mm, is finished by drenching with an aqueous solution of diisobutylphenoxyethoxyethyldimethylbenzylammonium chloride as cationic surfactant. The amount to be coated is adjusted through the concentration of the solution and through the quantity of liquid applied, as can be seen from the table. Then, drying takes place in an air drier at 100° C.

The finished non-woven fabric is tested for wick action (run-off) and rewet in accordance with the process described hereinbelow. The results are shown in the table below.

WICK ACTION (RUN-OFF) TEST

An absorbent cellulose pad weighing 300 g/m² and having a length of at least 250 mm is clamped with the covering non-woven fabric to be tested on a smooth impermeable substrate and placed at an angle of 45° C. to the perpendicular. At the upper end of the absorbent pad thus prepared, a discharge nozzle is mounted at a distance of 200 mm from the bottom end. This discharge nozzle is connected to an automatic 30-ml pipette. The discharge nozzle is designed so as to ensure a flow of 0.5 ml/sec in the above setup. Several layers of filter paper are placed underneath the bottom edge of the absorbent pad to collect the excess quantity. The 30 ml of the test liquid is then poured for 60 seconds from the pipette onto the absorbent pad. Distilled water is used as test liquid, the boundary surface force of which is adjusted to $42 \times 10^{-3}$ N/m at 23° C. by adding cationic surfactants. The stream of liquid first flows down along the surface of the covering non-woven fabric until wetting occurs. Then, the reat of the test liquid is picked up and stored by the absorbent pad. The excess test liquid, which reaches the bottom edge of the absorbent pad, is taken up by the filter paper placed therebelow and seized via differential paths. A good covering non-woven fabric should result in an excess of 0.5 g at the most. the less excess is collected at the bottom edge, the better the wick action.

REWET TEST

An absorbent cellulose pad having a weight per unit area of 300 g/m² is clamped over a smooth horizontal plate and covered with the non-woven fabric to be tested. A 20-mm tube with a diameter of 20 mm, on the bottom side of which a screen for distributing the liquid is located, is placed on the absorbent pad. Then, 30 ml of the test liquid indicated in the above run-off test is filled. After the liquid has been picked up by the absorbent pad, the wetted site is loaded for 3 minutes with a roller-shaped metal body weighing 30 N and having a contact surface of 100 cm². A filter paper folded several times is laid under the metal body and the wetted site is loaded for 2 more minutes. The liquid penetrating into the covering non-woven fabric is taken up by the filter paper and seized via differential paths. The result, termed "rewet", should be less than 1.0 g in the case of a non-woven fabric that still can be called "dry".

EXAMPLE 2

Under the conditions set forth in Example 1, a mixture of 80 weight percent methyldodecylbenzyltriammonium chloride and 20 weight percent methyldodecylxylylene-bis-(trimethylammonium chloride) is used as cationic surfactant. The results are listed in the table.

COMPARATIVE TEST

Under the conditions set forth in Example 1 and 2, a commercially available non-ionogenic surfactant is employed instead of the cationic surfactant embodying the invention. The result is likewise shown in the table.

TABLE 1

|  | Surfactant deposit in mg/surfactant/m² | Wick action (run-off) in g | Rewet in g |
|---|---|---|---|
| Example 1 |  |  |  |
| a | 25 | 0,17 | 0,18 |
| b | 50 | 0,12 | 0,22 |
| Example 2 |  |  |  |
| a | 25 | 0,21 | 0,17 |
| b | 50 | 0,02 | 0,26 |
| Comparative example |  |  |  |
| a | 25 | 0,65 | 0,70 |
|  | 50 | 0,20 | 1,80 |
|  | 75 | 0,14 | 2,20 |

We claim:
1. A non-woven fabric covering for absorbent cellulose material which comprises a surface-treated non-woven fabric, having a wick action, made up from synthetic fibers which are surface treated with an effective amount of a wetting agent, said wetting agent being capable of being chemisorbed on cellulose, said wetting agent being a cationic surfactant which causes a rapid transport of liquid to the absorbent cellulose materials while substantially blocking the return of the liquid to the fabric covering, said cationic surfactant having the formula:

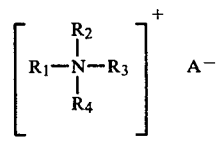

wherein $R_1$ to $R_4$ are chosen from the group consisting of alkyl of 1 to 20 carbon atoms, aryl, alkylaryl having 1 to 20 carbon atoms in the alkyl group, ethoxy, alkylethoxy having 1 to 20 carbon atoms in the alkyl group, arylethoxy, or alkylarylethoxy having 1 to 20 carbon atoms in the alkyl group, and A is an anion.

2. The non-woven fabric as recited in claim 1 wherein A is a halide.

3. A non-woven fabric as recited in claim 1 wherein $R_1$ to $R_4$ are chosen from the group consisting of: stearyldimethylbenzyl ammonium chloride, methyldodecylbenzyltrimethyl ammonium chloride, dodecyldimethylbenzylammonium chloride, tetradecyldimethylbenzylammoniumchloride, hexadecyldimethylbenzylammoniumchloride, diisobutylcresoxyethoxyethyldimethylbenzammoniumchloride, diisobutylphenoxyethoxyethyldimethylbenzylammoniumchloride, and methyldodecylxylylene-bis-(trimethylammonium chloride).

4. The non-woven fabric according to claims 1, wherein said wetting agent is employed in a quantity of 0.05 to 1.0 weight percent in relation to the weight of said non-woven fabric.

5. A process for manufacturing a surface-treated, non-woven fabric covering for absorbent cellulose materials which comprises:
(a) adding a cationic surfactant to a polymer melt to form a surfactant and polymer mix, said surfactant being characterized by the ability to cause a rapid transport of liquid to the absorbent cellulose materials while substantially blocking the return of the liquid to the fabric covering, said cationic surfactant having the formula:

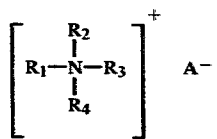

wherein $R_1$ to $R_4$ are chosen from the group consisting of alkyl of 1 to 20 carbon atoms, aryl, alkylaryl having 1 to 20 carbon atoms in the alkyl group, ethoxy, alkylethoxy having 1 to 20 carbon atoms in the alkyl group, arylethoxy, or alkylarylethoxy having 1 to 20 carbon atoms in the alkyl group, and A is an anion;

(b) extruding the surfactant and polymer mix using a conventional polymer fiber spinning and drawing means;

(c) solidifying the extruded surfactant and polymer mix by cooling to form filaments;

(d) laying down the filaments to form a non-woven mesh;

(e) bonding the filaments in the mesh to form a non-woven fabric.

* * * * *